United States Patent
Jarai et al.

(10) Patent No.: US 6,444,443 B1
(45) Date of Patent: Sep. 3, 2002

(54) GENE

(75) Inventors: Gabor Jarai, West Sussex (GB); Shida Yousefi, Bern (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/656,952

(22) Filed: Sep. 7, 2000

Related U.S. Application Data

(63) Continuation-in-part of application No. 09/575,302, filed on May 19, 2000, now abandoned.

(51) Int. Cl.[7] ............... C07H 21/04; C12P 21/02; C12N 1/20; C12N 15/00; C12N 15/12
(52) U.S. Cl. ............... 435/69.1; 435/252.3; 435/320.1; 530/350; 536/23.5
(58) Field of Search ................ 435/69.1; 536/23.5; 530/350

(56) References Cited

U.S. PATENT DOCUMENTS 5,958,726 A * 9/1999 Jacobs et al.

FOREIGN PATENT DOCUMENTS

| WO | WO 99/57144 | 11/1999 |
| WO | WO 99/63088 | 12/1999 |
| WO | WO 00/29574 | 5/2000 |

OTHER PUBLICATIONS

Mikayama et al, Molecular cloning and functional expression of a cDNA encoding gycosylation–inhibiting factor, Nov. 1993, Proc. Natl. Acad. Sci, USA vol. 90: 10056–10060.*

Voet et al., Biochemistry I, 1990, pp. 126–234.*

Attwood et al, The Babel of Bioinformatics, 2000, Science vol. 290 No. 5491: 471–473.*

Skolnick et al, From genes to protein structure and function: novel applications of computational approaches in the genomic era, Jan., 2000, TIBTECH 18:34–39.*

Ngo et al., in The Protein Folding Problem and Tertiary Structure Prediction, 1994, Merz, et al., (ed.), Birkhauser, Boston, MA, pp. 433 and 492–495).*

Wallace et al, Ologonucleotide Probes for the screening of recombinant DNA libraries, 1987, Methods Enzymol 152: 432–443.*

Sambrook et al, in Molecular Cloning A laboratory manual, 1989 second edition.*

Al–Shami et al., The Journal of Biological Chemistry, vol. 274, pp. 5333–5338 (1999).

Frazer et al., Journal of Immunological Methods, vol. 207, pp. 1–12 (1997).

Noguera et al., American Journal of Respiratory and Critical Care Medicine, vol. 158, pp. 1664–1668, (1998).

Verma et al., Nature 389: 239–242, Sep. 1997.

Darnell et al, in Molecular Cell Biology, by Scientific American Books, Inc, 1990, pp. 214–215.

* cited by examiner

*Primary Examiner*—Christina Chan
*Assistant Examiner*—Phuong N. Huynh
(74) *Attorney, Agent, or Firm*—David E. Wildman

(57) ABSTRACT

The invention provides an isolated inflammation-related gene, the protein molecule encoded by the gene, and the use of the gene in diagnosis and treatment of inflammatory conditions.

3 Claims, No Drawings

GENE

This application is a continuation-in-part of application Ser. No. 09/575,302 filed on May 19, 2000, now abandoned.

The present invention relates to a novel inflammation-related gene designated EXP189 encoding an intercellular adhesion molecule, and to the protein molecule encoded by EXP189. The invention also relates to the use of EXP189 polynucleotide sequences for diagnostic screening of patients and the use of the protein encoded by EXP189 as a therapeutic target.

Development and maintenance of several diseases, for example many respiratory and inflammatory diseases, involve the participation of a variety of cell types that undergo a number of phenotypic changes during the development of the pathological condition. These phenotypic alterations are the result of specific changes in the expression and functioning of various genes and proteins. The detection of genes or proteins, whose expression is altered in a particular physiological or pathological condition, can therefore lead to the identification of genes or proteins of pathological and therapeutical importance.

Cells that are attracted into tissues during inflammation include various inflammatory phagocytes such as neutrophilic and eosinophilic granulocytes and monocytes. These cells have been associated with inflammation and tissue destruction in several inflammatory diseases including respiratory tract inflammation in both acute and chronic bronchitis, chronic obstructive pulmonary disease (COPD), emphysema, asthma, adult respiratory distress syndrome (ARDS), rheumatoid arthritis, inflammatory bowel disease (IBD), ulcerative colitis, primary sclerosing cholangitis and Crohn's disease.

In several inflammatory respiratory diseases, there is an increased number of neutrophils present in the inflamed tissues. Enhanced migration into the lung, as a result of the release of chemoattractants by various leukocytes and epithelial cells, and the inhibition of apoptosis of these otherwise short-lived cells contribute to the accumulation of these cells at the sites of inflammation. Increased levels of granulocyte macrophage colony stimulating factor (GM-CSF) have been shown to increase the functional life span of neutrophils and to increase both phagocytic and oxidative burst activity and the production of proinflammatory cytokines that are critical for regulating the inflammatory process. The isolation of genes and proteins whose expression is upregulated upon cytokine stimulation, for example by GM-CSF, can identify molecular targets that can be exploited to offer therapeutic benefits.

Critical steps in the action of leukocytes in inflammatory conditions include the migration of these cells into the tissues, e.g. into the airways in respiratory inflammations or to the joints in rheumatoid arthritis, cell activation and the release of a range of inflammatory mediators, leukotrienes, oxygen radicals, proteases. Leukocyte migration involves the arrest and firm adhesion of blood cells on endothelial surfaces and the migration through the endothelium into the interstitium and from there to particular microenviroments. Several of these processes are dependent on the expression of cell surface adhesion molecules, which mediate the interaction of leukocytes for example with other cells of the same or different kind as well as with extracellular matrix components. The intercellular adhesion molecules expressed on the cell surface are thus involved in cell migration, tissue localisation and modification of cell function through downstream signalling events that can follow the engagement of the adhesion molecule with its ligand.

Recently, several methods and technologies have been developed for the detection of differential gene expression and the isolation of differentially expressed genes. For example, changes can be identified at the protein level using proteomics approaches and changes in transcriptional regulation can be detected by several methods including differential display (Liang, P., and Pardee, A. B., Science 257:967–971), SAGE (serial analyses of gene expression) (Velculescu, V. E., Zhang, L., Vogelstein, B., and Kinzler, K. W. Science, 270:484–487 ), differerential hybridization of complex cDNA probes high density cDNA or oligonucleotide arrays bound to solid support (Chee, M., Yang, R., Hubbell, E., Berno, A. Huang, X. C., Stern, D., Winkler,J., Lockhart, D. J., Morris, M. S. and Fodor, S. P. A. Science (1996) 274:610–614; Lockhart, D. J., Dong, H., Byrne,M. C., Follettie, M. T., Gallo, M. V., Chee, M. M., Wang, C., Kobayashi, M., Horton, H. and Brown, E. L. Nature Biotechnology (1996) 14:1675–1680; Shena, M., Shalon, D., Davis, R. W. and Brown, P. O. Science (1995) 250:467–470.) and cDNA subtraction methods such as representational difference analysis (Hubank, M., and Schatz, D. G. Nucleic Acids Res. 22: 5640–5648).

One method, which can be used to identify differentially expressed genes is Representational Difference Analysis of cDNA (cDNA-RDA). cDNA-RDA is a PCR-based subtractive enrichment procedure. Originally developed for the identification of differences between complex genomes it has been adapted to enable isolation of genes with altered expression between various tissues or cell samples (Lisitsyn, N., and Wigler, M. Science 259:946–951; Hubank, M., and Schatz, D. G. Nucleic Acids Res. 22: 5640–5648; O'Neill, M. J., and Sinclair, A. H. Nucleic Acids Res. 25: 2681–2682). This technique offers several advantages including the isolation of few false positives, the fact that unwanted difference products can be competitively eliminated and genes producing rare transcripts can also be detected and isolated.

Identification of novel genes that are expressed in neutrophils under inflammatory conditions would provide an important opportunity for the understanding of the inflammatory conditions from which a number of clinically important applications would arise. Novel genes and proteins identified may lead to the development of therapeutics (small molecule drugs, antisense molecules, antibody molecules) directly targeted to the gene or protein product of the gene, or may target the biochemical pathway at an upstream or downstream location if the development of such drugs is easier than directly targeting the gene. Polynucleotide sequences comprising the gene and sequence variants thereof may be used to develop a clinical diagnostic test for inflammatory conditions. Finally, information about the DNA sequences of the novel genes involved in inflammatory conditions and the amino acid sequences encoded by these genes facilitate large scale production of proteins by recombinant techniques and identification of the tissues and cells naturally producing the proteins. Such sequence information also permits the preparation of antibody substances or other novel binding molecules specifically reactive with the proteins encoded by the novel genes that may be used in modulating the natural ligand/antiligand binding reactions in which the proteins are involved.

Accordingly, the present invention provides, in one aspect, an isolated polynucleotide, hereinafter alternatively referred to as EXP189, comprising a nucleotide sequence encoding a polypeptide comprising the amino acid sequence of SEQ ID NO:2 or SEQ ID NO:19 or SEQ ID NO:20 or a functionally equivalent variant of said amino acid sequence, i.e. a variant thereof which retains the biological or other functional activity thereof, e.g. a variant which is capable of raising an antibody which binds to a polypeptide comprising the amino acid sequence of SEQ ID NO:2 or SEQ ID NO:19 or SEQ ID NO:20.

Terms used herein have the following meanings:

"Isolated" refers to material removed from its original environment.

"Hybridization" or "hybridizes" refers to any process by which a strand of a polynucleotide binds with a complementary strand through base pairing.

"Stringent conditions" refer to experimental conditions which allow up to 20% base pair mismatches, typically two 15 minute washes in 0.1 XSSC (15 mM NaCl, 1.5 mM sodium citrate, pH 7.0) at 65° C.

"Homology" or "homologous" refers to a degree of similarity between nucleotide or amino acid sequences, which may be partial or, when sequences are identical, complete.

"Expression vector" refers to a linear or circular DNA molecule which comprises a segment encoding a polypeptide of interest operably linked to additional segments which provide for its transcription.

"Antisense" refers to selective inhibition of protein synthesis through hybridisation of an oligo- or polynucleotide to its complementary sequence in messenger RNA (mRNA) of the target protein. The antisense concept was first proposed by Zamecnik and Stephenson (Proc. Natl. Acad. Sci. USA 75:280–284; Proc. Natl. Acad. Sci. USA 75:285–288) and has subsequently found broad application both as an experimental tool and as a means of generating putative therapeutic molecules (Alama, A., Pharmacol. Res. 36:171–178; Dean, N. M., Biochem. Soc. Trans. 24:623–629; Bennet, C. F., J. Pharmacol. Exp. Ther. 280:988–1000; Crooke, S. T., Antisense Research and Applications, Springer).

The term "variant" as used herein means, in relation to amino acid sequences, an amino acid sequence that is altered by one or more amino acids. The changes may involve amino acid substitution, deletion or insertion. In relation to nucleotide sequences, the term "variant" as used herein means a nucleotide sequence that is altered by one or more nucleotides; the changes may involve nucleotide substitution, deletion or insertion. A preferred functionally equivalent variant of the amino acid sequence SEQ ID NO:2 or SEQ ID NO:19 or SEQ ID NO:20 is one having at least 80%, more preferably at least 90%, and especially more than 95% amino acid sequence identity to SEQ ID NO:2 or SEQ ID NO:19 or SEQ ID NO:20 respectively.

By an amino acid sequence having x% identity to a reference sequence such as SEQ ID NO:2 or SEQ ID NO:19 or SEQ ID NO:20, is meant a sequence which is identical to the reference sequence except that it may include up to 100-x amino acid alterations per each 100 amino acids of the reference sequence. For example, in a subject amino acid sequence having at least 80% identity to a reference sequence, up to 20% of the amino acid residues in the reference sequence may be substituted, deleted or inserted with another amino acid residue. Percentage identity between amino acid sequences can be determined conventionally using known computer programs, for example the FASTDB program based on the algorithm of Brutlag et al (Comp.App.Biosci. (1990) 6:237–245).

The isolated polynucleotide of the invention may be cDNA, genomic DNA or RNA. In particular embodiments, the isolated polynucleotide is cDNA comprising the nucleotide sequence of SEQ ID NO:1 or SEQ ID NO:16 or SEQ ID NO:17 or SEQ ID NO:18 or a DNA comprising a nucleotide sequence which hybridises to SEQ ID NO:1 or SEQ ID NO:16 or SEQ ID NO:17 or SEQ ID NO:18 under stringent conditions. Nucleotide sequences which satisfy such hybridisation requirements include those resulting from deletions, insertions or substitutions of one or more nucleotides.

The invention also provides an isolated polynucleotide comprising a consecutive 20 base pair nucleotide portion identical in sequence to a consecutive 20 base pair portion of SEQ ID NO:1 or SEQ ID NO:16 or SEQ ID NO:17 or SEQ ID NO:18. In another aspect, the invention provides an isolated polynucleotide comprising a portion having at least 20, e.g. at least 50, e.g. at least 100, e.g. at least 200, contiguous bases from SEQ ID NO:1 or SEQ ID NO:16 or SEQ ID NO:17 or SEQ ID NO:18. In a further aspect, the invention provides an isolated polynucleotide comprising a nucleotide sequence encoding at least 10, e.g. at least 20, e.g. at least 50, e.g. at least 100, e.g. at least 200, contiguous amino acids from SEQ ID NO:2 or SEQ ID NO:19 or SEQ ID NO:20.

A polynucleotide of the invention may be isolated by (a) isolating a fragment thereof by subtracting cDNA species representing mRNA species present in resting neutrophil populations from cDNA species representing mRNA species present in neutrophils stimulated by GM-CSF, for example by using cDNA-RDA, and isolating the difference products, (b) sequencing the isolated fragment and (c) obtaining a full length clone by (i) first isolating overlapping fragments containing the 5' and 3' ends of the gene using 5' and 3' RACE (rapid amplification of cDNA ends) using gene specific primers designed using that sequence and RNA isolated from human cells, specifically from leukocytes or especially from phagocytes, e.g neutrophilic or eosinophilic granulocytes, and then joining those fragments together, e.g. by conventional methods, or (ii) by using the isolated fragment or a part thereof as probe for screening a human cDNA library, preferably a leukocyte or, especially, a granulocyte cDNA library, or a human genomic DNA library.

A polynucleotide of the invention may also be isolated by bioinformatics analysis of genomic DNA, cDNA and EST (expressed sequence tag) databases to identify a gene having a sequence having greater than 95% identity to the nucleotide sequence of SEQ ID NO:1 or SEQ ID NO:16 or SEQ ID NO:17 or SEQ ID NO:18 and isolating cDNA from a human cDNA library, preferably a leukocyte or, especially, a granulocyte cDNA library, by PCR using primers designed using that sequence, or by screening such a cDNA library using a probe designed using that sequence.

A polynucleotide of the invention, for example having the sequence SEQ ID NO:1 or SEQ ID NO:16 or SEQ ID NO:17 or SEQ ID NO:18, may be prepared from the nucleotides which it comprises by chemical synthesis, e.g. automated solid phase synthesis using known procedures and apparatus.

In another aspect, the present invention provides an isolated polypeptide, particularly a recombinant polypeptide, comprising the amino acid sequence of SEQ ID NO:2 or SEQ ID NO:19 or SEQ ID NO:20, or a functionally equivalent variant thereof. Such a polypeptide may be produced by cloning a polynucleotide sequence as hereinbefore described into an expression vector containing a promoter and other appropriate regulating elements for transcription, transferring into prokaryotic or eukaryotic host cells such as bacterial, plant, insect, yeast, animal or human cells, and culturing the host cells containing the recombinant expression vector under suitable conditions. Techniques for such recombinant expression of polypeptides are well known and are described, for example, in J.Sambrook et al, Molecular Cloning, second edition, Cold Spring Harbor Press, 1990.

Accordingly, the present invention also provides a method of producing a polypeptide of the invention which comprises culturing a host cell containing an expression vector containing a polynucleotide sequence of the invention as hereinbefore described under conditions suitable for expression of the polypeptide and recovering the polypeptide from the host cell culture.

In another aspect, the present invention provides an expression vector containing a polynucleotide sequence of the invention as hereinbefore described.

The invention also provides an isolated polypeptide comprising a consecutive 10 amino acid portion identical in sequence to a consecutive 10 amino acid portion of SEQ ID NO:2 or SEQ ID NO:19 or SEQ ID NO:20. In another aspect, the invention provides an isolated polypeptide comprising a portion having at least 10, e.g. at least 20, e.g. at least 50, e.g. at least 100, e.g. at least 200, contiguous amino acids from SEQ ID NO:2 or SEQ ID NO:19 or SEQ ID NO:20

A polypeptide of the invention may be expressed as a recombinant fusion protein with one or more heterologous polypeptides, for example to facilitate purification. For example, it may be expressed as a recombinant fusion protein with a heterologous polypeptide such as a polyhistidine containing a cleavage site located between the polynucleotide sequence of the invention and the heterologous polypeptide sequence, so that the polypeptide comprising the amino acid sequence of SEQ ID NO:2 or SEQ ID NO:19 or SEQ ID NO:20 may be cleaved and purified away from the heterologous moiety using well known techniques.

A polypeptide of the invention may also be synthesised, in whole or in part, from the amino acids which it comprises using well known chemical methods, for example automated solid phase techniques.

Isolated polypeptides of the invention as hereinbefore described may be purified by well known procedures.

The present invention also provides an antibody which is immunoreactive with a polypeptide of the invention as hereinbefore described. The antibody may be a polyclonal or monoclonal antibody. Such antibodies may be prepared using conventional procedures. Methods for the production of polyclonal antibodies against purified antigen are well established (cf. Cooper and Paterson in Current Protocols in Molecular Biology, Ausubel et al. Eds., John Wiley and Sons Inc., Chapter 11). Typically, a host animal, such as a rabbit, or a mouse, is immunised with a purified polypeptide of the invention, or immunogenic portion thereof, as antigen and, following an appropriate time interval, the host serum is collected and tested for antibodies specific against the polypeptide. Methods for the production of monoclonal antibodies against purified antigen are well established (cf. Chapter 11, Current Protocols in Molecular Biology, Ausubel et al. Eds., John Wiley and Sons Inc.). For the production of a polyclonal antibody, the serum can be treated with saturated ammonium sulphate or DEAE Sephadex. For the production of a monoclonal antibody, the spleen or lymphocytes of the immunised animal are removed and immortalised or used to produce hybridomas by known methods. Antibodies secreted by the immortalised cells are screened to determine the clones which secrete antibodies of the desired specificity, for example using Western blot analysis. Humanised antibodies can be prepared by conventional procedures.

In another aspect, the present invention provides an antisense oligonucleotide comprising a nucleotide sequence complementary to that of a polynucleotide of the invention, in particular a nucleotide sequence complementary to SEQ ID NO:1 or SEQ ID NO:16 or SEQ ID NO:17 or SEQ ID NO:18. The antisense oligonucleotide may be DNA, an analogue of DNA such as a phosphorothioate or methylphosphonate analogue of DNA, RNA, an analogue of RNA, or a peptide nucleic acid (PNA). The antisense oligonucleotides may be synthesised by conventional methods, for example using automated solid phase techniques.

The present invention also provides a polynucleotide probe comprising at least 15 contiguous nucleotides of a polynucleotide of the invention or a complement thereof. The probe may be cDNA, genomic DNA or RNA. Usually it is a synthetic oligonucleotide comprising 15 to 50 nucleotides, which can be labelled, e.g. with a fluorophore, to provide a detectable signal.

The polynucleotide probe is capable of selectively hybridising under stringent conditions to a polynucleotide fragment having a sequence SEQ ID NO:1 or SEQ ID NO:16 or SEQ ID NO:17 or SEQ ID NO:18. The probe has a sequence such that under such hybridisation conditions it hybridizes only to its cognate sequence. DNA probes as described above are useful in a number of screening applications including Northern and Southern blot analyses, dot blot and slot blot analyses, and fluorescence in situ hybridisation (FISH).

The present invention also includes a pair of oligonucleotides having nucleotide sequences useful as primers for DNA amplification of a fragment of a polynucleotide of the invention, i.e. of EXP189, wherein each primer of said pair is at least 15 nucleotides in length and said pair have sequences such that when used in a polymerase chain reaction (PCR) with either human genomic DNA or a suitable human cDNA target they result in synthesis of a DNA fragment containing all or preferably part of the sequence of EXP189. The primer pair is preferably capable of amplifying the coding region of EXP189 or portion thereof. Examples of such primer pairs are shown hereinafter as SEQ ID NOs 3–4 and SEQ ID NOs 5–6 respectively.

The role of the polypeptide of the invention in asthma and other obstructive or inflammatory airways diseases characterised by neutrophilic or eosinophilic inflammation can be determined using conventional allergen driven animal models for inflammatory conditions, e.g. an ovalbumin-induced mouse or rat model.

Polynucleotides, polypeptides, antibodies, antisense oligonucleotides or probes of the invention as hereinbefore described, hereinafter alternatively referred to collectively as agents of the invention, may be used in the treatment (prophylactic or symptomatic) or diagnosis of inflammatory diseases, particularly inflammatory or obstructive airways diseases. For example, a polypeptide of the invention may be used to treat a mammal, particularly a human, deficient in or otherwise in need of that polypeptide; a polynucleotide of the invention may be used in gene therapy where it is desired to increase EXP189 activity, for instance where a subject has a mutated or missing EXP189 gene; an antisense oligonucleotide of the invention may be used to inhibit EXP189 activity, where this is desired; an antibody of the invention may be used to detect, or determine the level of expression of, EXP189 polypeptides, or to inhibit ligand/antiligand binding activities of EXP189 polypeptides; and a probe of the invention may be used to detect the presence or absence of the EXP189 gene, i.e. to detect genetic abnormality.

"Gene therapy" refers to an approach to the treatment of human disease based upon the transfer of genetic material into somatic cells of an individual. Gene transfer can be achieved directly in vivo by administartion of gene-bearing viral or non-viral vectors into blood or tissues, or indirectly ex vivo through the introduction of genetic material into cells manipulated in the laboratory followed by delivery of the gene-containing cells back to the individual. By altering the genetic material within a cell, gene therapy may correct underlying disease pathophysiology. Suitable vectors, and procedures, for gene delivery to specific tissues and organ systems in animals are described in Dracopoli, N. C. et al., Current Protocols in Human Genetics. John Wiley and Sons Inc., Chapters 12 and 13 respectively. In relation to polynucleotides of the invention, gene therapy may involve delivery of a viral or non-viral gene therapy vector containing an expression cassette of the EXP189 gene under suitable control elements to the lungs of diseased individuals so that the underlying disease pathophysiology is corrected or ameliorated.

Accordingly, in further aspects, the present invention provides

- a pharmaceutical composition comprising a polynucleotide, polypeptide, antibody, polynucleotide probe or antisense oligonucleotide of the invention as hereinbefore described, optionally together with a pharmaceutically acceptable carrier;
- a method of treating an inflammatory disease, particularly an inflammatory or obstructive airways disease which comprises administering to a subject in need thereof an effective amount of a polynucleotide, polypeptide, antibody or antisense oligonucleotide of the invention as hereinbefore described;
- a method of detecting genetic abnormality or predisposition to developing a disease in a subject which comprises incubating a genetic sample from the subject with a polynucleotide probe of the invention as hereinbefore defined, under conditions where the probe hybridises to complementary polynucleotide sequence, to produce a first reaction product, and comparing the first reaction product to a control reaction product obtained with a normal genetic sample, where a difference between the first reaction product and the control reaction product indicates a genetic abnormality in the subject or a predisposition to developing a disease;
- a method of detecting the presence of a polynucleotide of the invention, e.g. comprising SEQ ID NO:1 or SEQ ID NO:16 or SEQ ID NO:17 or SEQ ID NO:18, in cells or tissues which comprises contacting DNA from the cell or tissue with a polynucleotide probe as hereinbefore defined under conditions where the probe is specifically hybridizable with a polynucleotide of the invention, and detecting whether hybridization occurs;
- a method of detecting an abnormality in the nucleotide sequence of a polynucleotide of the invention in a patient which comprises amplifying a target nucleotide sequence in DNA isolated from the patient by a polymerase chain reaction using a pair of primers as hereinbefore described which target the sequence to be amplified and analysing the amplified sequence to determine any polymorphism present therein;

The term "polymorphism" means any sequence difference as compared with the sequence of a polynucleotide of the invention as hereinbefore described.

Hybridisation of a polynucleotide probe of the invention with complementary polynucleotide sequence may be detected using in situ (eg. FISH) hybridization, Northern or Southern blot analyses, dot blot or slot blot analyses. The abnormality may also be detected for example by conformation sensitive gel electrophoresis (CSGE) and DNA sequencing as described hereinafter in the Examples. The genetic abnormality may result in a change in the amino acid sequence of the individual's EXP189 protein relative to the amino acid sequence of a normal EXP189 protein, or loss of protein. Alternatively, the change may not alter the amino acid sequence but may instead alter expression of the EXP189 gene by altering the sequence of controlling elements either at the 5'-, or 3'-end of the gene, or altering the sequence of control elements within intronic regions of the gene. Changes may also affect the way the gene transcript is processed or translated. The invention also includes kits for the detection of an abnormality in the polynucleotide sequence of an individual's EXP189 gene. Hybridisation kits for such detection comprise a probe of the invention as hereinbefore described, which probe may be modified by incorporation of a detectable, e.g. chemiluminescent or fluorescent, label therein, and may include other reagents such as labelling reagents, i.e. reagents to incorporate a detectable label such as a radioactive isotope, chemiluminescent or fluorescent group into a hybridised product, and buffers. PCR amplification kits comprise primer pairs such as those described above together with a DNA polymerase such as Taq polymerase, and may include additional reagents, such as an amplification buffer and the like. Specific embodiments of the PCR amplification kits can include additional reagents specific for a number of techniques that detect polynucleotide changes, including CSGE and DNA sequencing.

The effectiveness of an agent of the invention in inhibiting or reversing inflammatory conditions, for example in inflammatory airways diseases, may be demonstrated in an animal model, e.g. a mouse or rat model, of airways inflammation or other inflammatory conditions, for example as described by Szarka et al, J. Immunol. Methods (1997) 202:49–57; Renzi et al, Am. Rev. Respir. Dis. (1993) 148:932–939; Tsuyuki et al., J. Clin. Invest. (1995) 96:2924–2931; Cernadas et al (1999) Am. J. Respir. Cell Mol. Biol. 20:1–8; Durie et al., Clin. Immunol. Immunopathol.(1994) 73: 11–18; and Williams et al., Proc. Natl. Acad. Sci. USA (1992) 89:9784–9788.

Inflammatory diseases to which the present invention is applicable include inflammatory or obstructive airways diseases such as asthma of whatever type or genesis, including both intrinsic (non-allergic) asthma and extrinsic (allergic) asthma. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Other inflammatory or obstructive airways diseases and conditions to which the present invention is applicable include adult respiratory distress syndrome (ARDS), chronic obstructive pulmonary or airways disease (COPD or COAD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their anti-inflammatory activity, in particular in relation to inhibition of neutrophil or eosinophil activation, agents of the invention are also useful in the treatment of neutrophil or eosinophil related disorders, e.g. neutrophilia or eosinophilia, in particular neutrophil or eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction; and neutrophil-related disorders such as acute and chronic bronchitis, COPD, ARDS, emphysema, rheumatoid arthritis, inflammatory bowel disease (IBD), ulcerative colitis, primary sclerosing cholangitis and Crohn's disease.

The agents of the invention may be administered by any appropriate route, e.g. orally, for example in the form of a tablet or capsule; parenterally, for example intravenously; topically, e.g. in an ointment or cream; transdermally, e.g. in a patch; by inhalation; or intranasally.

Pharmaceutical compositions containing agents of the invention may be prepared using conventional diluents or excipients and techniques known in the galenic art. Thus oral dosage forms may include tablets and capsules, and compositions for inhalation may comprise aerosol or other atomizable formulations or dry powder formulations.

The invention includes (A) an agent of the invention in inhalable form, e.g. in an aerosol or other atomizable composition or in inhalable particulate, e.g. micronised form, (B) an inhalable medicament comprising an agent of the invention in inhalable form; (C) a pharmaceutical product comprising such an agent of the invention in inhalable form in association with an inhalation device; and (D) an inhalation device containing an agent of the invention in inhalable form.

Dosages of agents of the invention employed in practising the present invention may of course vary depending, for example, on the particular condition to be treated, the effect desired and the mode of administration. In general, suitable daily dosages for administration by inhalation are of the order of 1 µg/kg to 10 mg/kg while for oral administration suitable daily doses are of the order of 0.1 mg/kg to 1000 mg/kg.

A polypeptide of the invention can be used to identify substances that can act as enhancers (agonists) or inhibitors (antagonists) of its activity, i.e. to identify compounds useful in the treatment of inflammatory diseases. Accordingly, the invention also provides a method of identifying a substance which modulates the activity of a polypeptide of the invention comprising combining a candidate substance with a polypeptide of the invention and measuring the effect of the candidate substance on said activity. The activity of a polypeptide of the invention may be measured, for example, by measuring intracellular siganalling events, by an appropriate reporter gene assay or by a cellular assay, e.g. by a cellular adhesion assay. The invention also includes a method of identifying a substance which binds to a polypeptide of the invention comprising mixing a candidate substance with a polypeptide of the invention and determining whether binding has occurred.

The invention is illustrated by the following Examples. Abbreviations used in the Examples have the following meanings:

BLAST: basic local alignment search tool
BSA: bovine serum albumin
cAMP: cyclic adenosine monophosphate
DTT: dithiothreitol
EDTA: ethylenediamine tetra acetic acid
EIA: enzyme immunoassay
EST: expressed sequence tag
FCS: fetal calf serum
GM-CSF: granulocyte macrophage colony stimulating factor
HEPES: 4-(2-hydroxyethyl)piperazine-1-ethanesulfonic acid
IPTG: isopropyl-b-D-thiogalactopiranoside
LMP: low melting point
MOI: multiplicity of infection
PBS: phosphate buffered saline
PEG: polyethylene glycol
PBMC: peripheral blood mononuclear cells
PCR: polymerase chain reaction
PMSF: phenylmethylsulfonyl fluoride
RPMI: Rosewell Park Memorial Institute
SDS-PAGE: sodium dodecyl sulfate polyacrylamide gel electrophoresis
TEV: tobacco etch virus

EXAMPLE 1

Blood (200 ml) is collected in tubes containing sodium citrate under sterile conditions from normal donors with no history of respiratory diseases. Neutrophils are purified by well established methods. PBMC are separated from peripheral blood cells by Ficoll Hypaque (Pharmacia) centrifugation. The remaining cell population, mainly granulocytes and erythrocytes, are treated with erythrocyte lysis solution (155 mM $NH_4Cl$, 10 mM $KHCO_3$, 0.1 mM EDTA, PH 7.3). To determine the purity, granulocytes are stained with Hansel stain (Difco Laboratories Ltd) and are differentiated by light microscopy at high power magnification. The contamination with eosinophils is found to be less than 2%. For stimulation, neutrophils are resuspended at a concentration of 5 million cells per ml in RPMI-1640 plus 10% FCS. Cells are cultured for 5 hours with or without 50 ng/ml human recombinant GM-CSF (R&D System). Total RNA is extracted using TRIZOL Reagent (Gibco/BRL) as described by the manufacturer. One ml of TRIZOL is used for resuspension of every 5 million pelleted neutrophils. mRNA is purified using the MESSAGEMAKER mRNA isolation kit (Gibco/BRL) using conditions recommended by the manufacturer. 300 ng of mRNA is used to synthesize cDNA using the Superscript Choice System (Gibco/BRL) and oligo(dT) primer for first strand synthesis. Double stranded cDNA is extracted once with an equal volume of phenol:chloroform:isoamyl alcohol and precipitated with 0.5 volume 7.5 M ammonium acetate and 2.5 volumes of ethanol. Following centrifugation the resultant pellet is washed with 70% ethanol and resuspended in 16 mµl of sterile water.

The resulting cDNA samples are used in the cDNA subtraction and selective enrichment procedures for the isolation of genes preferentially expressed upon GM-CSF stimulation in neutrophils.

EXAMPLE 2

This Example describes the generation of a subtracted library by cDNA-RDA and the isolation of an EXP189 cDNA clone.

cDNA-RDA is performed essentially as described by Hubank, M., and D. G. Schatz. Nucleic Acids Res. 22: 5640–5648; and O'Neill, M. J., and A. H. Sinclair. Nucleic Acids Res. 25: 2681–2682. Double stranded cDNA samples prepared from mRNA isolated from unstimulated and stimulated neutrophils are digested with DpnII restriction enzyme and ligated to R-adaptors obtained by annealing a 24 mer (SEQ ID NO:7) to a 12 mer (SEQ ID NO:8) oligonucleotide. Amplicons for both 'tester' (cDNA of stimulated neutrophils) and 'driver' (cDNA of unstimulated neutrophils) are generated using Expand Long Template PCR System and Expand Buffer 1 (Roche Diagnostics). Typically, five 100 µl PCRs for each tester and ten for each driver are performed. DpnII digestion is used to remove the R-adaptors from both driver and tester amplicons. J-adaptors, obtained by annealing a 24 mer (SEQ ID NO:9) to a 12 mer (SEQ ID NO:10) are then ligated to the tester population. Subtractive hybridizations are performed in 5 mµl reactions at 67° C. for 20 hours. To generate difference product one (DP1) 250 ng of tester cDNA is mixed with 25 µg of driver cDNA at a ratio of 100:1. DP1 cDNA is then digested with DpnII to remove J-adaptors prior to ligation of N-adaptors, that are obtained by annealing a 24 mer (SEQ ID NO:11) to a 12 mer (SEQ ID NO:12) oligonucleotide. To generate difference product two (DP2) 31.25 ng of tester is mixed with 25 µg of driver cDNA at a ratio of 800:1. Digested and excess adaptors are removed by washing the cDNA on Microcon 30 filters (Amicon). The subtracted library is fractionated by agarose gel electrophoresis. Fractions in 1.5% LMP agarose gels are digested with Agarase (Roche Diagnostics) at 42° C. overnight, washed three times with sterile water and concentrated using Microcon 30 filters (Amicon). Prior to ligation, the subtracted PCR cDNA mix is incubated for 20 minutes with additional dATP and Taq DNA polymerase (Roche Diagnostics) to ensure that most of the cDNA fragments contain 'A overhangs'. Approximately 10 ng of cDNA is ligated to 25 ng pCR2.1 vector (Invitrogen) and the ligation introduced into 50 µl One Shot competent cells (Invitrogen). The libraries are plated onto agar plates containing 50 µg/ml carbenicillin, and 100 mM IPTG and 50 µg/ml X-Gal. Plates are incubated at 37° C. overnight and then briefly at 4° C. to allow blue/white staining to be clearly distinguishable and plasmids are purified from 3 ml cultures of the white colonies. Inserts of individual clones are analysed by determining their nucleotide sequence on an automated ABI310 sequencer (Perkin-Elmer) using M13 reverse and forward primers. The resulting sequences are analysed in sequence similarity searches using the BLAST algorithm and sequence alignments are done using the GCG software package (Wisconsin Package Version 9.1). A clone called EXP189 is identified as containing an insert with no significant sequence similarity to any database entries. The full length EXP189 gene is then isolated by RACE (rapid amplification of cDNA ends). The 3' and 5' ends of the EXP189 gene are obtained using cDNA isolated from peripheral blood neutrophils and gene-specific primers designed using the sequence of the insert in the EXP189 clone. The primer sequences are shown in SEQ ID NO: 13 and NO: 14. RACE is carried out using the 5' RACE system kit and the 3' RACE system kit of Life Technologies as suggested by the manufacturer. Amplification products are analysed by determining their nucleotide sequences on both strands on an automated ABI310 sequencer (Perkin-Elmer) using M13 reverse and forward primers as well as gene specific primers. The resulting sequences are analysed and sequence contig is obtained using the GCG software package (Wisconsin Package Version 9.1). The obtained cDNA sequence contig is shown in SEQ ID NO:1 and is called clone 1. By sequencing multiple RACE products other variants of the EXP189 gene are also identified. One of these variants lacks an A residue at position 971 in SEQ ID NO:1 and this sequence variant is shown in SEQ ID NO:17 and is called clone 2. Another variant of the EXP189 gene is characterized by the lack of an A residue at position 971 and a deletion of 30 nucleotides between positions 1049 and 1078 in the sequence shown in SEQ ID NO:1 as shown in SEQ ID NO:18 and is called clone 3.

EXAMPLE 3

This Example relates to the prediction of the function of the EXP189 protein using in silico approaches.

The DNA sequences of the various forms of EXP189 obtained in Example 2 and shown in SEQ ID NOS:1, 16, 17 and 18 are used to deduce the amino acid sequence of the different EXP189 proteins. The amino acid sequences of EXP189 are tested using various bioinformatics applications including sequence similarity searches, determination of the secondary stucture of the protein and identification of functional domains. Translation of the cDNA sequence shown in SEQ ID NO:1 generates a protein of 318 amino acid residues shown in SEQ ID NO:2. Translation of the cDNA sequence shown in SEQ ID NO:17 generates a protein of 344 amino acid residues as shown in SEQ ID NO:19 and translation of the cDNA sequence shown in SEQ ID NO:18 generates a protein of 394 amino acid residues as shown in SEQ ID NO:20. It is found that all three variants of the EXP189 protein contain an approximately 19 amino acid long signal sequence at the N-terminus allowing for the membrane localization and/or secretion of the EXP189 protein, two extracellular IgG like domains located approximately between residues 37–118 and 150–236, an approximately 20 amino acid long membrane spanning domain between residues 276–296. The intracellular tail at the C terminus of the EXP189 protein varies between the various forms identified.The protein shown in SEQ ID NO:2 has a short, approximately 22 amino acid residue intracellular tail. The other EXP189 variant proteins shown in SEQ ID NO:19 and SEQ ID NO:20 have an intracellular tail of approximately 48 and 98 amino acid residues, respectively. The differences in the intracellular part of the EXP189 protein may have functional consequences for example in the context of intracellular signaling. The overall structure and many of the structural features and sequence similarity to proteins such as the myelin p0 protein indicate that the EXP189 protein is involved in the intercellular adhesion of cells that express it on their surface.

EXAMPLE 4

This Example relates to the expression of the full length EXP189 clone 1 with a 6 histidine tag after the ATG start codon using the Baculovirus system in *Spodoptera frugiperda* Sf9 cells, and to the purification of the resulting polypeptide.

Construction of a Recombinant EXP189 Baculovirus

A unique EcoRI site is incorporated 5' to the EXP189 start codon (ATG) by PCR amplification using the following primer (SEQ ID NO:15):

5'- TTGAAAGTTGAATTCAGCATGTTTTGCCCA-CTGA-3'

Another primer is used to introduce a unique XbaI (TCTAGA) site 3' to the Exp189 stop codon (TAA, reverse complement: TTA (SEQ ID NO:16):

5'-GGGTTTTTCTAGAATCTCTGGTTAGTCTTCTTC-GTG-3'

The recombinant amplified product is digested with EcoRI and XbaI restricion enzymes and ligated as a 979 bp fragment into EcoRI/XbaI digested pFastbac™HTa baculovirus transfer vector (Life Technologies). In this construct the EXP189 gene is expressed as a fusion potein as the EXP189 coding region is placed after a 6x His affinity tag followed by a spacer region, a recognition site for TEV protease and an additional 7 amino acid linker region. Expression of the EXP189 fusion protein containing the 6x His tag aids affinity purification and the TEV protease cleavage site is used to remove the 6x His tag. The recombinant EXP189 sequence is transposed into Bacmid DNA carried by DH10Bac cells (Life Technologies; Bac to Bac Baculovirus expression system). EXP189 recombinant Bacmids are isolated from DH10Bac cells and successful transposition is confirmed by PCR analyses.

Transfection of Sf9 Cells with Recombinant EXP189 Bacmid DNA and Amplification of Recombinant Baculovirus Stocks Recombinant EXP189 Bacmid DNA is transfected into Sf9 cells using published protocols (Bac to Bac baculovirus expression system manual; Life Technologies). Recombinant baculoviruses are harvested from the culture medium after 3-day incubation at 27° C. The cell supernatants are clarified by centrifugation for 5 min at 500×g and kept at 4° C. The recombinant Baculovirus is amplified by infecting Sf9 cells (SF900 SFMII medium; Life Technologies) at a cell density of $1 \times 10^6$ cells/ml and a multiplicity of infection (MOI) of 0.01 for 48 hours. Sf9 cells are then centrifuged at 1000×g for 5 minutes. The supernatants containing high titre virus are stored at 4° C.

Expression of Recombinant EXP189 in Sf9 Cells

Sf9 cells, maintained at densities of between $2 \times 10^5$ and $3 \times 10^6$ cells/ml in SF900 SFMII medium; Life Technologies) in either shaker flasks (rotated at 90 RPM) or spinner flasks (stirring at 75 RPM) are infected with the amplified recombinant Baculovirus at a cell density of $1.5 \times 10^6$ at an MOI of 2.0 for 60 hours. Following infection Sf9 cells are centrifuged at 1000×g for 5 minutes, the supernatants poured off and the cell pellets frozen at −80° C.

Crude Lysate Preparation

The cells ($1 \times 10^9$) are resuspended in 100 ml lysis buffer (20 mM Hepes pH 7.9, 100 mM NaCl, 5% glycerol, 2 mM E-mercaptoethanol, 0.5 mM imidazole, 0.1% Nonidet P-40, 40 pg/ml AEBSF, 0.5 pg/ml leupeptin, 1 pg/ml aprotinin and 0.7 pg/ml pepstatin A). Cells are incubated on ice for 15 minutes then centrifuged at 39,000×g for 30 minutes at 4° C.

Metal Chelate Affinity Chromatography

Metal chelate affinity chromatography is carried out at room temperature with a column attached to a BioCAD chromatography workstation. A 20 ml Poros MC/M (16mmD×100 mmL) column is charged with $Ni^{2+}$ prior to use and after each injection. To charge with $Ni^{2+}$, the column is washed with 10 column volumes (CV) 50 mM EDTA pH 8, 1 M NaCl followed by 10 CV water. The column is charged with 500 ml 0.1 M NiSO4 pH 4.5–5, washed with 10 CV water, then any unbound $Ni^{2+}$ removed by washing with 5 CV 0.3 M NaCl. All steps are performed with a flow rate of 20 ml/min. The charged MC/M column is equilibrated with 5 CV Buffer B (20 mM Hepes pH 7.9, 100 mM NaCl, 5% glycerol, 2 mM E-mercaptoethanol, 1 mM PMSF, 100 mM imidazole) to saturate the sites followed by 10 CV Buffer A (as Buffer B except 0.5 mM imidazole). 90–95 ml of the crude lysate is loaded onto the column per run at a flow rate of 20 ml/min. Subsequent steps are carried out with a flow rate of 30 ml/min. Any unbound material is removed by washing with 12 CV buffer A and EXP189 eluted by applying a 0–50% Buffer B gradient over 10 CV. Fractions (8 ml) are collected over the gradient. EXP189 containing fractions are combined and protease inhibitors added to the final concentrations described for the lysis buffer above. DTT is also added to a final concentration of 1 mM. The combined fractions are dialysed overnight against 4 litres 20 mM Hepes pH 7.9, 1 mM DTT, 0.2 mM PMSF at 4° C. The protein concentartion is determined and, if needed, samples are concentrated using a Millipore Ultrafree-15 centrifugation device (MW cut-off 50 kDa) at 4° C. The device is pre-rinsed with water prior to use. The final storage buffer used for long term storage at −80° C. is 20 mM Hepes pH 7.9, 1 mM DTT, ~100 mM NaCl, 5% glycerol. Glycerol can be omitted from the sample for storage at 4° C.

EXAMPLE 5

This example relates to the generation of polyclonal antibodies against the EXP189 protein prepared as described in Example 4.

Immunisation

Rabbits are immunised at 4 subcutaneous sites with 500 μg purified EXP189 protein according to the following schedule:

| DAYS | IMMUNISATIONS |
|---|---|
| 0 | 1st immunisation 1:1 in complete Freund's adjuvant |
| 15 | 1st boost 1:1 in incomplete Freund's adjuvant |
| 45 | 2nd boost 1:1 in incomplete Freund's adjuvant |
| 55 | 1st test bleed from the ear artery |
| Every month | Boost 1:1 in incomplete Freund's adjuvant until a good antibody response is obtained |

Test bleeds (500 μl) are taken and the serum assessed for antibody titre. Serum is collected when a maximum titre is reached. This is done by collecting blood (10 ml) and allowing it to clot for 2 hours at 4° C. The blood is centrifuged at 1000×g for 5 minutes to separate the serum. The serum is removed and stored at −20° C. until assayed.

ELISA Screening

Nunc-Immuno Plate Maxisorp 96 well plates (Nunc, Basle, CH) are used as a solid support and coated with the purified EXP189 protein (100 ng/well) overnight at 4° C. The plates are blocked for 3 hours at 37° C. with PBS containing 2% BSA (Sigma) and 0.02% $NaN_3$ (Sigma). After blocking, plates are incubated overnight at room temperature with plasma in different dilutions of PBS. The presence of polyclonal antibodies is checked with both biotin labelled IgG-antibodies to rabbit (Goat anti-rabbit IgG antiserum, 1:25000 dilution), with an incubation time of 40 minutes. Alkaline phosphatase conjugated streptavidin (Immununo Research, Dianova, CH) is then added at a dilution of 1:10000. Development of the reaction is carried out by adding phosphate substrate (Sigma, f.c. 1 mg/ml) dissolved in diethanolamine. After 45 minutes, absorbance is read at 405 nm with a reference of 490 nm with an ELISA plate reader (Biorad).

Purification of the Polyclonal Antibodies 5 ml protein A-agarose is poured into a chromatography column and washed with 6 column volumes of 0.1 M tris (hydroxymethyl) methylamine (Tris) buffer pH 7.5. The rabbit serum containing anti- EXP189 antibodies is diluted (1/2) with Tris buffer and added to the protein A-agarose. Unbound proteins are removed by washing the column with 6 volumes of Tris buffer. The IgG is eluted off the column with three column volumes of 0.1 M glycine buffer pH 3.0 and collected as 1 ml fractions into tubes containing 28 µl of 1 M Tris. The fractions which are positive for protein content are checked for purity by SDS-PAGE under reducing conditions. Two bands at 50 and 25 Kd are visualised corresponding to the heavy and light chains of an immunoglobulin molecule. Fractions containing only immunoglobulin are pooled, re-checked for protein concentration and stored at −20° C.

EXAMPLE 6

This example relates to the generation of monoclonal antibodies against the EXP189 protein prepared as described in Example 4.

Immunisation

Female Balb/c mice are immunised intraperitoneally (ip) with 100 µg of EXP189 protein according to the schedule given below:

| DAYS | IMMUNISATIONS |
| --- | --- |
| 1 | 1$^{st}$ immunisation 1:1 with complete Freund's adjuvant |
| 14 | 1$^{st}$ boost 1:1 with incomplete Freund's adjuvant |
| 21 | 2$^{nd}$ boost 1:1 with incomplete Freund's adjuvant |
| 28–30 | Three final boosts in PBS |
| 31 | Fusion with mouse myeloma cells |

Serum is assessed for antibody titre by ELISA (Example 5) after the animal is sacrificed for the preparation of spleen cells for fusion. If antibody titre is sufficient, (1/1000 to 1/100,000), the hybridomas are screened, otherwise discarded.

Preparation of Myeloma Cells

Sp2/0 murine myeloma cells (ATCC #CRL 1581; maintained in culture medium containing 20 µg/ml 8-azaguanine) are cultivated for one week before fusion in RPMI 1640 (8-azaguanine is not included), 10% (v/v) FCS and 1% penicillin-streptomycin (50 IU/ml and 50 µg/ml, respectively). The cells are harvested by centrifugation (200×g for 5 minutes) and washed three times in cold RPMI 1640. Approximately 2.5×10$^6$ cells are used per 96 well microtitre plate.

Preparation of Spleen Cell Suspension

The mouse is killed by an overdose of anesthetic (Forene), the spleen dissected and pressed through a cell strainer (70 µm mesh cell strainer; Becton & Dickinson, Oxford, UK, Cat. No 2350). The cell suspension is washed three times in RPMI 1640 (as above) and counted: 5.10$^6$ cells/96 well plate are necessary.

Fusion of Myeloma Cells and Spleen Cells

The spleen and myeloma cells are mixed (2:1), centrifuged (200×g for 5 min) and the pellet warmed in a 37° C. water bath. Prewarmed polyethylene glycol 4000 (1 ml per 10$^8$ cells) is added slowly over one minute, then 20 ml of prewarmed wash medium over two minutes. After centrifugation the pellet is carefully resuspended in selection medium (RPMI 1640, 10% FCS, 1% penicillin-streptomycin, 10% BM condimed H1 (feeder cell replacement from Boehringer Mannheim, Lewes, UK; Cat. No. 1 088 947), 10 % HAT-media supplement (hypoxanthine, aminopterin and thymidine to select against unfused myeloma cells; Boehringer Mannheim, Lewes, UK; Cat. No. 644 579) and plated, 200 µl/well of a 96 well microtitre plate.

After five days clusters of hybrid cells can be identified by examining the bottom of the microtitre wells with an inverted microscope. After 10–14 days the culture supernatant is tested for the presence of antibodies by ELISA (Example 5). The positive clones are expanded in a 24 well assay plate and retested.

Cloning of Positive Hybridomas

The expanded clones which are still positive are cloned by limiting dilution. Cells are diluted serially in four dilutions steps in a 96 well microtitre plate; 5, 2, 1 and 0.5 cells/well. HAT-media supplement is replaced with HT-media supplement (Boehringer Mannheim, Lewes, UK; Cat. No. 623 091). After approximately one week the cells are screened by ELISA (Example 5). The cells of those wells containing a single positive clone are expanded.

Production of Monoclonal Antibody Supernatant

The cells are grown in culture flasks in standard medium (RPMI 1640, 10% (v/v) FCS and 1% penicillin-streptomycin) until the hybridomas overgrow and die. The debris is removed by centrifugation and the supernatant containing the antibodies is titred using ELISA (Example 5) before storing under sterile conditions at 4° C., −20° C. or −70° C.

What is claimed is:

1. An isolated polynucleotide comprising a nucleotide sequence encoding a polypeptide comprising the amino acid sequence set forth in SEQ ID NO:19 or SEQ ID NO:20.

2. A method of producing a polypeptide which comprises culturing a host cell containing an expression vector comprising an isolated polynucleotide of claim 1, expressing a polypeptide encoded by the isolated polynucleotide of claim 1 by the host cell culture, and recovering the polypeptide from the host cell culture.

3. An expression vector comprising an isolated polynucleotide of claim 1.

* * * * *

SEQUENCE LISTING

<160> NUMBER OF SEQ ID NOS: 20

<210> SEQ ID NO 1
<211> LENGTH: 1592

```
<212> TYPE: DNA
<213> ORGANISM: Homo sapiens

<400> SEQUENCE: 1
gcccttgtgc tcttcatctt ggatttgaaa gttgagagca gcatgttttg cccactgaaa      60
ctcatcctgc tgccagtgtt actggattat accttgggcc tgaatgactt gaatgttttcc    120 ccgcctgagc taacagtcca tgtgggtgat tcagctctga tgggatgtgt tttccagagc    180
acagaagaca aatgtatatt caagatagac tggactctgt caccaggaga gcacgccaag    240
gacgaatatg tgctatacta ttactccaat ctcagtgtgc ctattgggcg cttccagaac    300
cgcgtacact tgatggggga caacttatgc aatgatggct ctctcctgct ccaagatgtg    360
caagaggctg accagggaac ctatatctgt gaaatccgcc tcaagggga gagccaggtg     420 ttcaggaagg cggtggtact gcatgtgctt ccagaggagc ccaaagagct catggtccat    480
gtgggtggat tgattcagat gggatgtgtt ttccagagca cagaagtgaa acacgtgacc    540
aaggtagaat ggatattttc aggacggcgc gcaaggagg agattgtatt tcgttactac     600
cacaaactca ggatgtctgc ggagtactcc cagagctggg gccacttcca gaatcgtgtg    660
aacctggtgg gggacatttt ccgcaatgac ggttccatca tgcttcaagg agtgagggag    720
tcagatggag gaaactacac ctgcagtatc cacctaggga acctggtgtt caagaaaacc    780
attgtgctgc atgtcagccc ggaagagcct cgaacactgg tgaccccggc agccctgagg    840
cctctggtct tgggtggtaa tcagttggtg atcattgtgg gaattgtctg tgccacaatc    900
ctgctgctcc ctgttctgat attgatcgtg aagaagacct gtggaaataa gagttcagtg    960
aattctacag atcttggtga agaacacgaa gaagactaat ccagagataa agaaaaaacc   1020
ctgccatttt gaaagatgtg aaggggaggt gaacacacgc ttcagcctaa aacactaaaa    1080
acacatttac tccccaataa ttgtacggga ggtgatcgag gaagaagaac caagtgaaaa    1140
atcagaggcc acctacatga ccatgcaccc agtttggcct tctctgaggt cagatcggaa   1200
caactcactt gaaaaaaagt caggtgggg aatgccaaaa acacagcaag cctttgaga    1260 agaatggaga gtcccttcat ctcagcagcg gtggagactc tctcctgtgt gtgtcctggg   1320
ccactctacc agtgatttca gactcccgct ctcccagctg tcctcctgtc tcattgtttg   1380
gtcaatacac tgaagatgga gaatttggag cctggcagag agactggaca gtctggagga   1440
acaggcctgc tgaggggagg ggagcatgga cttggcctct ggagtgggac actggccctg   1500
ggaaccaggc tgagctgagt ggcctcaaac ccccgttgg atcagaccct cctgtgggca    1560
gggttcttag tggatgagtt actgggaagg gc                                1592

<210> SEQ ID NO 2
<211> LENGTH: 318
<212> TYPE: PRT
<213> ORGANISM: Homo sapiens

<400> SEQUENCE: 2

Met Phe Cys Pro Leu Lys Leu Ile Leu Leu Pro Val Leu Leu Asp Tyr
 1               5                  10                  15

Thr Leu Gly Leu Asn Asp Leu Asn Val Ser Pro Pro Glu Leu Thr Val
                20                  25                  30

His Val Gly Asp Ser Ala Leu Met Gly Cys Val Phe Gln Ser Thr Glu
            35                  40                  45

Asp Lys Cys Ile Phe Lys Ile Asp Trp Thr Leu Ser Pro Gly Glu His
        50                  55                  60
```

-continued

```
Ala Lys Asp Glu Tyr Val Leu Tyr Tyr Ser Asn Leu Ser Val Pro
 65                  70                  75                  80

Ile Gly Arg Phe Gln Asn Arg Val His Leu Met Gly Asp Asn Leu Cys
             85                  90                  95

Asn Asp Gly Ser Leu Leu Leu Gln Asp Val Gln Glu Ala Asp Gln Gly
            100                 105                 110

Thr Tyr Ile Cys Glu Ile Arg Leu Lys Gly Glu Ser Gln Val Phe Arg
            115                 120                 125

Lys Ala Val Val Leu His Val Leu Pro Glu Glu Pro Lys Glu Leu Met
130                 135                 140

Val His Val Gly Gly Leu Ile Gln Met Gly Cys Val Phe Gln Ser Thr
145                 150                 155                 160

Glu Val Lys His Val Thr Lys Val Glu Trp Ile Phe Ser Gly Arg Arg
            165                 170                 175

Ala Lys Glu Glu Ile Val Phe Arg Tyr Tyr His Lys Leu Arg Met Ser
            180                 185                 190

Ala Glu Tyr Ser Gln Ser Trp Gly His Phe Gln Asn Arg Val Asn Leu
            195                 200                 205

Val Gly Asp Ile Phe Arg Asn Asp Gly Ser Ile Met Leu Gln Gly Val
210                 215                 220

Arg Glu Ser Asp Gly Gly Asn Tyr Thr Cys Ser Ile His Leu Gly Asn
225                 230                 235                 240

Leu Val Phe Lys Lys Thr Ile Val Leu His Val Ser Pro Glu Glu Pro
            245                 250                 255

Arg Thr Leu Val Thr Pro Ala Ala Leu Arg Pro Leu Val Leu Gly Gly
            260                 265                 270

Asn Gln Leu Val Ile Ile Val Gly Ile Val Cys Ala Thr Ile Leu Leu
            275                 280                 285

Leu Pro Val Leu Ile Leu Ile Val Lys Lys Thr Cys Gly Asn Lys Ser
            290                 295                 300

Ser Val Asn Ser Thr Asp Leu Gly Glu Glu His Glu Glu Asp
305                 310                 315
```

<210> SEQ ID NO 3
<211> LENGTH: 21
<212> TYPE: DNA
<213> ORGANISM: Homo sapiens

<400> SEQUENCE: 3
agcacgccaa ggacgaatat g                                          21

<210> SEQ ID NO 4
<211> LENGTH: 22
<212> TYPE: DNA
<213> ORGANISM: Homo sapiens

<400> SEQUENCE: 4
tatcagaaca gggagcagca gg                                         22

<210> SEQ ID NO 5
<211> LENGTH: 22
<212> TYPE: DNA
<213> ORGANISM: Homo sapiens

<400> SEQUENCE: 5
cactgaaact catcctgctg cc                                         22

```
<210> SEQ ID NO 6
<211> LENGTH: 20
<212> TYPE: DNA
<213> ORGANISM: Homo sapiens

<400> SEQUENCE: 6
ttgcggaaaa tgtcccccac                                              20

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: adaptor
      sequence

<400> SEQUENCE: 7
agcactctcc agcctctcac cgca                                         24

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence: adaptor
      sequence

<400> SEQUENCE: 8
gatctgcggt ga                                                      12

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: adaptor
      sequence

<400> SEQUENCE: 9
accgacgtcg actatccatg aaca                                         24

<210> SEQ ID NO 10
<211> LENGTH: 12
<212> TYPE: DNA
<213> ORGANISM: Artificial Sequence
<220> FEATURE:
<223> OTHER INFORMATION: Description of Artificial Sequence: adaptor
      sequence

<400> SEQUENCE: 10
gatctgttca tg                                                      12

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: adaptor
      sequence

<400> SEQUENCE: 11
aggcaactgt gctatccgag ggaa                                         24

<210> SEQ ID NO 12
<211> LENGTH: 12
<212> TYPE: DNA
<213> ORGANISM: Artificial Sequence
```

```
<220> FEATURE:
<223> OTHER INFORMATION: Description of Artificial Sequence: adaptor
      sequence

<400> SEQUENCE: 12
gatcttccct cg                                                              12

<210> SEQ ID NO 13
<211> LENGTH: 26
<212> TYPE: DNA
<213> ORGANISM: Homo sapiens

<400> SEQUENCE: 13
gtcaggtggg ggaatgccaa aaacac                                               26

<210> SEQ ID NO 14
<211> LENGTH: 27
<212> TYPE: DNA
<213> ORGANISM: Homo sapiens

<400> SEQUENCE: 14
gcaggcctgt tcctccagac tgtccag                                              27

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: primer
      designed to clone the  EXP189 protein into
      expression vector

<400> SEQUENCE: 15
ttgaaagttg aattcagcat gttttgccca ctga                                      34

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: primer
      designed to amplify and clone EXP189 sequence into
      expression vector

<400> SEQUENCE: 16 gggttttttct agaatctctg gttagtcttc ttcgtg                                   36

<210> SEQ ID NO 17
<211> LENGTH: 1591
<212> TYPE: DNA
<213> ORGANISM: Homo sapiens

<400> SEQUENCE: 17
gcccttgtgc tcttcatctt ggatttgaaa gttgagagca gcatgttttg cccactgaaa          60
ctcatcctgc tgccagtgtt actggattat accttgggcc tgaatgactt gaatgttttcc       120 ccgcctgagc taacagtcca tgtgggtgat tcagctctga tgggatgtgt tttccagagc        180
acagaagaca aatgtatatt caagatagac tggactctgt caccaggaga gcacgccaag        240
gacgaatatg tgctatacta ttactccaat ctcagtgtgc ctattgggcg cttccagaac        300
cgcgtacact tgatggggga caacttatgc aatgatggct ctctcctgct ccaagatgtg        360
caagaggctg accagggaac ctatatctgt gaaatccgcc tcaaagggga gagccaggtg        420
ttcaggaagg cggtggtact gcatgtgctt ccagaggagc ccaaagagct catggtccat        480
```

| | |
|---|---|
| gtgggtggat tgattcagat gggatgtgtt ttccagagca cagaagtgaa acacgtgacc | 540 |
| aaggtagaat ggatatttc aggacggcgc gcaaaggagg agattgtatt tcgttactac | 600 |
| cacaaactca ggatgtctgc ggagtactcc cagagctggg gccacttcca gaatcgtgtg | 660 |
| aacctggtgg gggacatttt ccgcaatgac ggttccatca tgcttcaagg agtgagggag | 720 |
| tcagatggag gaaactacac ctgcagtatc cacctaggga acctggtgtt caagaaaacc | 780 |
| attgtgctgc atgtcagccc ggaagagcct cgaacactgg tgaccccggc agccctgagg | 840 |
| cctctggtct tgggtggtaa tcagttggtg atcattgtgg gaattgtctg tgccacaatc | 900 |
| ctgctgctcc ctgttctgat attgatcgtg aagaagacct gtggaaataa gagttcagtg | 960 |
| aattctacag tcttggtgaa gaacacgaag aagactaatc cagagataaa agaaaaaccc | 1020 |
| tgccatttg aaagatgtga agggaggtg aacacacgct tcagcctaaa acactaaaaa | 1080 |
| cacatttact ccccaataat tgtacgggag gtgatcgagg aagaagaacc aagtgaaaaa | 1140 |
| tcagaggcca cctacatgac catgcaccca gtttggcctt ctctgaggtc agatcggaac | 1200 |
| aactcacttg aaaaaagtc aggtgggga atgccaaaaa cacagcaagc cttttgagaa | 1260 |
| gaatggagag tcccttcatc tcagcagcgg tggagactct ctcctgtgtg tgtcctgggc | 1320 |
| cactctacca gtgatttcag actcccgctc tcccagctgt cctcctgtct cattgtttgg | 1380 |
| tcaatacact gaagatggag aatttggagc ctggcagaga gactggacag tctggaggaa | 1440 |
| caggcctgct gaggggaggg gagcatggac ttggcctctg gagtgggaca ctggccctgg | 1500 |
| gaaccaggct gagctgagtg gcctcaaacc ccccgttgga tcagaccctc ctgtgggcag | 1560 |
| ggttcttagt ggatgagtta ctgggaaggg c | 1591 |

<210> SEQ ID NO 18
<211> LENGTH: 1561
<212> TYPE: DNA
<213> ORGANISM: Homo sapiens

<400> SEQUENCE: 18

| | |
|---|---|
| gcccttgtgc tcttcatctt ggatttgaaa gttgagagca gcatgttttg cccactgaaa | 60 |
| ctcatcctgc tgccagtgtt actgattat accttgggcc tgaatgactt gaatgttcc | 120 |
| ccgcctgagc taacagtcca tgtgggtgat tcagctctga tgggatgtgt tttccagagc | 180 |
| acagaagaca aatgtatatt caagatagac tggactctgt caccaggaga gcacgccaag | 240 |
| gacgaatatg tgctatacta ttactccaat ctcagtgtgc ctattgggcg cttccagaac | 300 |
| cgcgtacact tgatggggga caacttatgc aatgatggct ctctcctgct ccaagatgtg | 360 |
| caagaggctg accagggaac ctatatctgt gaaatccgcc tcaagggga gagccaggtg | 420 |
| ttcaggaagg cggtggtact gcatgtgctt ccagaggagc ccaaagagct catggtccat | 480 |
| gtgggtggat tgattcagat gggatgtgtt ttccagagca cagaagtgaa acacgtgacc | 540 |
| aaggtagaat ggatatttc aggacggcgc gcaaaggagg agattgtatt tcgttactac | 600 |
| cacaaactca ggatgtctgc ggagtactcc cagagctggg gccacttcca gaatcgtgtg | 660 |
| aacctggtgg gggacatttt ccgcaatgac ggttccatca tgcttcaagg agtgagggag | 720 |
| tcagatggag gaaactacac ctgcagtatc cacctaggga acctggtgtt caagaaaacc | 780 |
| attgtgctgc atgtcagccc ggaagagcct cgaacactgg tgaccccggc agccctgagg | 840 |
| cctctggtct tgggtggtaa tcagttggtg atcattgtgg gaattgtctg tgccacaatc | 900 |
| ctgctgctcc ctgttctgat attgatcgtg aagaagacct gtggaaataa gagttcagtg | 960 |

-continued

```
aattctacag tcttggtgaa gaacacgaag aagactaatc cagagataaa agaaaaaccc    1020
tgccattttg aaagatgtga aggggagaaa cacatttact ccccaataat tgtacgggag    1080
gtgatcgagg aagaagaacc aagtgaaaaa tcagaggcca cctacatgac catgcaccca    1140
gtttggcctt ctctgaggtc agatcggaac aactcacttg aaaaaaagtc aggtggggga    1200
atgccaaaaa cacagcaagc ttttgagaa gaatggagag tcccttcatc tcagcagcgg    1260
tggagactct ctcctgtgtg tgtcctgggc cactctacca gtgatttcag actcccgctc    1320
tcccagctgt cctcctgtct cattgtttgg tcaatacact gaagatggag aatttggagc    1380
ctggcagaga gactggacag tctggaggaa caggcctgct gaggggaggg gagcatggac    1440
ttggcctctg gagtgggaca ctggcccctgg gaaccaggct gagctgagtg gcctcaaacc    1500
ccccgttgga tcagaccctc ctgtgggcag ggttcttagt ggatgagtta ctgggaaggg    1560
c                                                                    1561
```

<210> SEQ ID NO 19
<211> LENGTH: 344
<212> TYPE: PRT
<213> ORGANISM: Homo sapiens

<400> SEQUENCE: 19

```
Met Phe Cys Pro Leu Lys Leu Ile Leu Leu Pro Val Leu Leu Asp Tyr
  1               5                  10                  15

Thr Leu Gly Leu Asn Asp Leu Asn Val Ser Pro Pro Glu Leu Thr Val
                 20                  25                  30

His Val Gly Asp Ser Ala Leu Met Gly Cys Val Phe Gln Ser Thr Glu
             35                  40                  45

Asp Lys Cys Ile Phe Lys Ile Asp Trp Thr Leu Ser Pro Gly Glu His
         50                  55                  60

Ala Lys Asp Glu Tyr Val Leu Tyr Tyr Ser Asn Leu Ser Val Pro
     65                  70                  75                  80

Ile Gly Arg Phe Gln Asn Arg Val His Leu Met Gly Asp Asn Leu Cys
                 85                  90                  95

Asn Asp Gly Ser Leu Leu Leu Gln Asp Val Gln Glu Ala Asp Gln Gly
            100                 105                 110

Thr Tyr Ile Cys Glu Ile Arg Leu Lys Gly Glu Ser Gln Val Phe Arg
        115                 120                 125

Lys Ala Val Val Leu His Val Leu Pro Glu Glu Pro Lys Glu Leu Met
    130                 135                 140

Val His Val Gly Gly Leu Ile Gln Met Gly Cys Val Phe Gln Ser Thr
145                 150                 155                 160

Glu Val Lys His Val Thr Lys Val Glu Trp Ile Phe Ser Arg Arg
                165                 170                 175

Ala Lys Glu Glu Ile Val Phe Arg Tyr Tyr His Lys Leu Arg Met Ser
            180                 185                 190

Ala Glu Tyr Ser Gln Ser Trp Gly His Phe Gln Asn Arg Val Asn Leu
        195                 200                 205

Val Gly Asp Ile Phe Arg Asn Asp Gly Ser Ile Met Leu Gln Gly Val
    210                 215                 220

Arg Glu Ser Asp Gly Gly Asn Tyr Thr Cys Ser Ile His Leu Gly Asn
225                 230                 235                 240

Leu Val Phe Lys Lys Thr Ile Val Leu His Val Ser Pro Glu Glu Pro
                245                 250                 255

Arg Thr Leu Val Thr Pro Ala Ala Leu Arg Pro Leu Val Leu Gly Gly
```

-continued

```
                260                 265                 270
Asn Gln Leu Val Ile Ile Val Gly Ile Val Cys Ala Thr Ile Leu Leu
            275                 280                 285

Leu Pro Val Leu Ile Leu Ile Val Lys Lys Thr Cys Gly Asn Lys Ser
        290                 295                 300

Ser Val Asn Ser Thr Val Leu Val Lys Asn Thr Lys Thr Asn Pro
305                 310                 315                 320

Glu Ile Lys Glu Lys Pro Cys His Phe Glu Arg Cys Glu Gly Glu Val
                325                 330                 335

Asn Thr Arg Phe Ser Leu Lys His
            340

<210> SEQ ID NO 20
<211> LENGTH: 394
<212> TYPE: PRT
<213> ORGANISM: Homo sapiens

<400> SEQUENCE: 20

Met Phe Cys Pro Leu Lys Leu Ile Leu Leu Pro Val Leu Leu Asp Tyr
  1               5                  10                  15

Thr Leu Gly Leu Asn Asp Leu Asn Val Ser Pro Pro Glu Leu Thr Val
             20                  25                  30

His Val Gly Asp Ser Ala Leu Met Gly Cys Val Phe Gln Ser Thr Glu
         35                  40                  45

Asp Lys Cys Ile Phe Lys Ile Asp Trp Thr Leu Ser Pro Gly Glu His
     50                  55                  60

Ala Lys Asp Glu Tyr Val Leu Tyr Tyr Tyr Ser Asn Leu Ser Val Pro
 65                  70                  75                  80

Ile Gly Arg Phe Gln Asn Arg Val His Leu Met Gly Asp Asn Leu Cys
                 85                  90                  95

Asn Asp Gly Ser Leu Leu Leu Gln Asp Val Gln Glu Ala Asp Gln Gly
            100                 105                 110

Thr Tyr Ile Cys Glu Ile Arg Leu Lys Gly Glu Ser Gln Val Phe Arg
        115                 120                 125

Lys Ala Val Val Leu His Val Leu Pro Glu Glu Pro Lys Glu Leu Met
130                 135                 140

Val His Val Gly Gly Leu Ile Gln Met Gly Cys Val Phe Gln Ser Thr
145                 150                 155                 160

Glu Val Lys His Val Thr Lys Val Glu Trp Ile Phe Ser Gly Arg Arg
                165                 170                 175

Ala Lys Glu Glu Ile Val Phe Arg Tyr Tyr His Lys Leu Arg Met Ser
            180                 185                 190

Ala Glu Tyr Ser Gln Ser Trp Gly His Phe Gln Asn Arg Val Asn Leu
        195                 200                 205

Val Gly Asp Ile Phe Arg Asn Asp Gly Ser Ile Met Leu Gln Gly Val
    210                 215                 220

Arg Glu Ser Asp Gly Gly Asn Tyr Thr Cys Ser Ile His Leu Gly Asn
225                 230                 235                 240

Leu Val Phe Lys Lys Thr Ile Val Leu His Val Ser Pro Glu Glu Pro
                245                 250                 255

Arg Thr Leu Val Thr Pro Ala Ala Leu Arg Pro Leu Val Leu Gly Gly
            260                 265                 270

Asn Gln Leu Val Ile Ile Val Gly Ile Val Cys Ala Thr Ile Leu Leu
        275                 280                 285
```

-continued

```
Leu Pro Val Leu Ile Leu Ile Val Lys Lys Thr Cys Gly Asn Lys Ser
    290             295             300
Ser Val Asn Ser Thr Val Leu Val Lys Asn Thr Lys Lys Thr Asn Pro
305             310             315             320
Glu Ile Lys Glu Lys Pro Cys His Phe Glu Arg Cys Glu Gly Glu Lys
            325             330             335
His Ile Tyr Ser Pro Ile Ile Val Arg Glu Val Ile Glu Glu Glu Glu
            340             345             350
Pro Ser Glu Lys Ser Glu Ala Thr Tyr Met Thr Met His Pro Val Trp
            355             360             365
Pro Ser Leu Arg Ser Asp Arg Asn Asn Ser Leu Glu Lys Lys Ser Gly
    370             375             380
Gly Gly Met Pro Lys Thr Gln Gln Ala Phe
385             390
```